United States Patent [19]

Rosenberg

[11] 4,382,783
[45] May 10, 1983

[54] INTRAORAL DENTAL APPLIANCE TO CORRECT RETRUSIVE MANDIBLES ORTHOPEDICALLY IN THE TREATMENT OF CLASS II MALOCCLUSIONS

[76] Inventor: Farel A. Rosenberg, 10535 Wilshire Blvd., Los Angeles, Calif. 90024

[21] Appl. No.: 392,898

[22] Filed: Jun. 28, 1982

[51] Int. Cl.³ .............................................. A61C 7/00
[52] U.S. Cl. ...................................................... 433/19
[58] Field of Search ..................................... 433/18, 19

[56] References Cited

U.S. PATENT DOCUMENTS 3,798,773  3/1974  Northcutt .............................. 433/19

FOREIGN PATENT DOCUMENTS 1110363  12/1960  Fed. Rep. of Germany ........ 433/19

*Primary Examiner*—Robert Peshock
*Attorney, Agent, or Firm*—Gilbert Kivenson

[57] ABSTRACT

An orthopedic appliance for improving or correcting the overbite and overjet of persons having an abnormal, Class II relationship between the maxillary (upper jaw) and mandibular (lower jaw) bones and their respective teeth, where the mandible and its teeth are posteriorly displaced. Two hinges with telescoping members are used to join an upper molar and lower molar on both sides of the mouth. The point of attachment of each lower hinge is somewhat forward on the lower molar than the corresponding point on the upper molar when the appliance is installed so that closure of the mouth forces the lower jaw forward. In children, and adults to a limited extent, this produces permanent, "muscle-resting length" changes and also induces growth and changes of the lower jaw and its joint. As a result, there is a permanent correction of the occlusions to a normal, Class I bite after the appliance is worn for a period of time.

7 Claims, 12 Drawing Figures (a)

(b)

(c)

INTRAORAL DENTAL APPLIANCE TO CORRECT RETRUSIVE MANDIBLES ORTHOPEDICALLY IN THE TREATMENT OF CLASS II MALOCCLUSIONS

BACKGROUND OF THE INVENTION

This invention relates to orthopedic appliances for correcting Class II malocclusion in children and adults in which the upper row of teeth are found considerably ahead of the lower row. Class II malocclusion produces an abnormal bite and detracts from the individual's appearance. Orthodontists correct this situation by slowly moving teeth under pressure, accompanied at times by the extraction of certain teeth and in some cases retarding maxillary growth to bring the upper and lower rows of teeth into an alignment more suitable for efficient and comfortable mastication. This process of moving teeth - "orthodontics" may be accomplished by the use of a wire fastened to each tooth in either or both the upper and lower dental arches. These arrangements, called arch wires, exert forces on the teeth which gradually induce them to move into the desired position. Aside from orthodontics, one method of improving the mandible-maxilla relationship is to couple the upper and lower jaws with various types of linkages so that natural closing and opening movements of the patient during speaking and chewing, force the lower jaw (the mandible) into an improved position with respect to the upper jaw (the maxilla). The opening or closing forces of the jaw muscles are thus utilized to bring about the desired correction. Because a permanent change in the positional relationship of the jawbones, rather than the movement of individual teeth is accomplished, this practice is termed "dental orthopedics". Some appliances for this purpose have employed rubber bands or springs so arranged that opening of the mouth tends to draw the lower jaw forward. Another approach has been the use of telescoping but rigid linkages between the upper and lower jaws which push the latter forward when the mouth is closed. Devices which draw the lower jaw forward are taught in U.S. Pat. Nos. 3,618,214 and 3,654,702. Appliances for pushing the lower jaw forward are described by E. Herbst in the magazine "Rundschau", Volume 34, Page 1515, published in 1934, and by M. Northcutt in U.S. Pat. No. 3,798,773 issued in 1971.

A problem with pulling devices has been their inability to produce more than nominal forces on the lower jaw. The force capability of the jaw muscles is much greater when the mouth is being closed than when it is being opened. Another problem with the pulling type of appliance is that the maximum force is exerted when the mouth is wide open. The normal position of the lower jaw during waking hours is such that the mouth is just slightly open. The linkages which induce forward motion of the lower jaw by pulling are therefore less effective than the pushing type.

Pushing appliances as devised by Herbst and Northcutt produce good results but are of relatively large size. Because they are attached to a limited number of teeth in the mandible, prior art pushing devices strongly tend to push the lower anterior teeth (as well as the jaw) forward, an undesirable effect. In addition, they require at least one laboratory fabrication step or possibly more, as the case demands, thus increasing dental chair time in preparation for laboratory models, bite measurements, etc. Another problem with the Herbst and Northcutt appliances, is their difficulty of adjustment once cemented. A further problem involves the linkage which, if too short, may cause the device to become disassembled in the patient's mouth during unexpected "over opening". Furthermore, these appliances inhibit lateral jaw movement. During the months that the patient must wear the appliance, there are continuous occasions when side to side movement must be made. Any limitation of this mobility increases the discomfort of wearing the appliance. It is also important to note that uninterrupted orthodontic treatment of all the teeth does not lend itself to these methods of orthopedic correction because the appliance does not permit the simultaneous use of full continuous arch wires. This shortcoming of the prior art prolongs treatment time because both processes cannot be concurrent.

The present invention overcomes the objection of limited lateral movement by the use of pivoting to achieve mobility in three planes and thus increases patient comfort. The invention also provides a convenient method for adjustment in the patient's mouth without the cutting of metal or the involvement of additional laboratory work. Also, the design of the appliance minimizes the possibility of accidental disassembly while it is in the patient's mouth. It may be used separately as is now done with the Herbst appliance but, more importantly, this invention permits continuous and simultaneous orthodontic treatment during the orthopedic correction and is totally convertible -- i.e., it may be inserted or removed at any time during the orthodontic phase without disturbing installed arch wires.

In another embodiment of the invention, provision is made to assure corrective action during sleep, a hitherto overlooked method for shortening treatment time.

Still another embodiment of the invention permits precision adjustment in the patient's mouth to provide corrective forces exactly suited to the individual.

SUMMARY OF THE INVENTION

In this invention, two telescoping, expandable, pivoted hinges join the upper and lower sets of teeth on the right and left sides of the mouth, at the first molars or teeth functioning as first molars. Considerable horizontal force can be exerted on the lower jaw by the invention to achieve a normal, Class I position from its retruded Class II starting point. This force can be adjusted by the orthodontist during installation to suit each individual case. These forward, corrective forces are exerted automatically on the mandible on a continuous basis as long as they remain installed in the mouth, and increase to a maximum when full closure is reached.

BRIEF DESCRIPTION OF THE DRAWINGS

FIG. 2 (b) is an enlarged view of the linkage.

DESCRIPTION OF THE INVENTION

Figure 1:
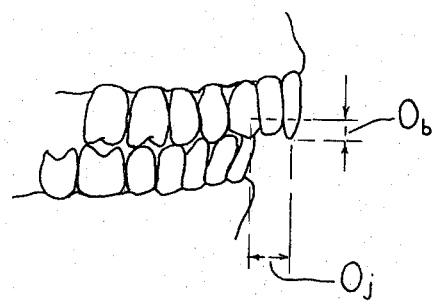
FIG. 1 is a right side view of one case of malocclusion.

FIG. 1, which illustrates an exaggerated form of Class II malocclusion, also shows the two common and undesirable conditions which exist under these circumstances. Because of retrusion of the mandible there is an exaggerated "overjet" $O_j$. This is accompanied by the second abnormal condition, the excessive "overbite" $O_b$. These abnormalities interfere with proper functioning and also detract from the person's appearance. It has been found that continuously forcing the mandible forward involuntarily for a period of months achieves a satisfactory and lasting orientation between upper and lower rows of teeth. The lower jaw is thus permanently corrected into a forward position. The present invention accomplishes this with a hinged telescoping linkage as will now be described.

Figure 2A:
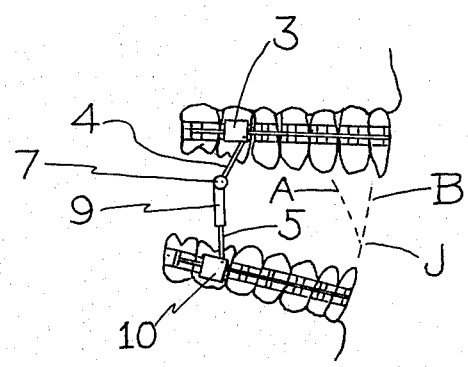
FIG. 2 (a) is a right side view of the teeth of FIG. 1 showing one pair of linkages made and installed in accordance with the principles of the invention. The invention is attached to tubes welded to molar bands, which are in turn secured by cementing to upper and lower first molars or to teeth functioning as first molars.
Figure 2B:
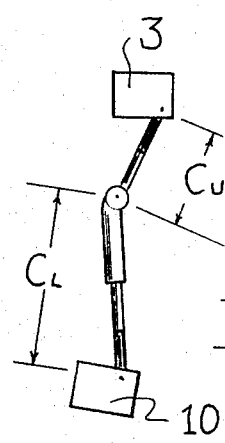
Figure 3:
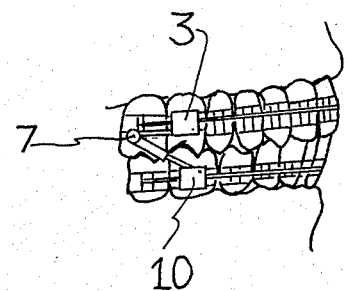
FIG. 3 is a side view of the teeth in FIG. 2 (a) when the mouth is closed, showing the mandibular teeth in their now-corrected forward position, i.e., the normal Class I occlusion achieved by the invention.

Referring next to FIG. 2 (a), a cylinder 9 is pivoted to an upper link 4 forming a hinge joint at point 7. Piston 5, which also serves as a lower link, fits loosely into cylinder 9 and is pivoted in lower mounting block 10. Upper link 4 is similarly pivoted to an upper mounting block 3. The combined piston and cylinder length $C_L$ in the lower part of the linkage (FIG. 2 (b) is somewhat longer than $C_U$, the length of link 4. As the mouth is closing, link 4 comes to rest in its mounting block 3 while the piston 5 is still free to move. Further closing of the mouth then drives piston 5 home to the cylinder base and finally results in forward pressure which pushes the lower jaw forward. The closure path of the lower jaw without the appliance is shown at A in FIG. 2 (a); the effect of the appliance is to change the path to that shown at B. The point of path modification J occurs when the upper link 4 seats in its mounting block 3.

Figure 4:
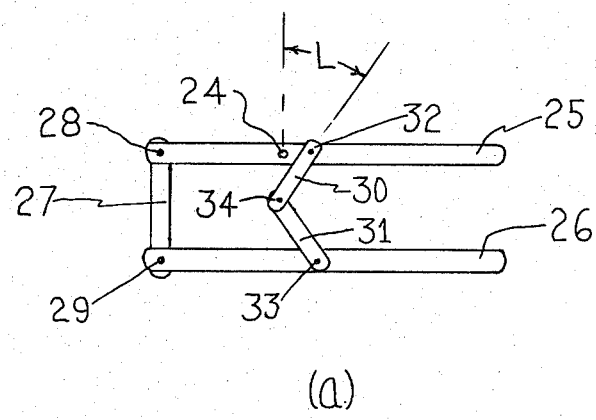
FIG. 4 is a bar linkage diagram to explain, in simpler terms, the general principle of the invention.
Figure 4:
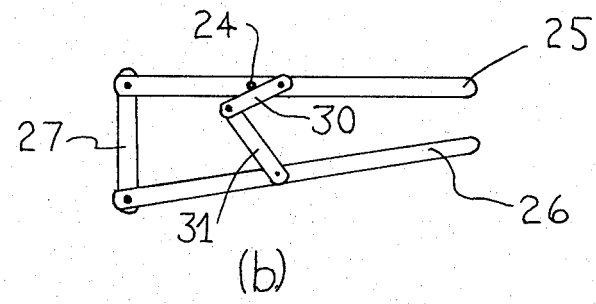
Figure 4:
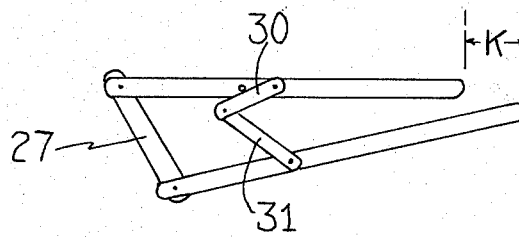

A simplified model of the jaw structure will now be used to further explain the functioning of the invention. In FIG. 4 (a) the upper and lower jaws are represented by the bars 25 and 26 respectively. The natural hinge structure of the jaw is hypothetically simulated by the bar 27 and pins 28 and 29. The invention is modelled by the links 30 and 31, the pins 32, 33 and 34 and the stop 24. The latter determines the upper limit of travel of link 30 about pin 32 and simulates the bottoming of the invention's link into its upper mounting block. When the lower bar 26 is moved upward, with the upper bar 25 held immobile, the links 30 and 31 fold. There is little horizontal displacement of bar 26, FIG. 4 (b). When stop 24 is contacted by link 30, however, further upward motion of bar 26 can only involve link 31 and bar 27. The result is a horizontal displacement of bar 26 as shown by K in FIG. 4 (c). The angular movement of link 30 has been restricted to the angle L as seen in FIG. 4 (a). The angle L can be controlled by varying the length of the link 30 or the position of the stop 24.

Figure 5:
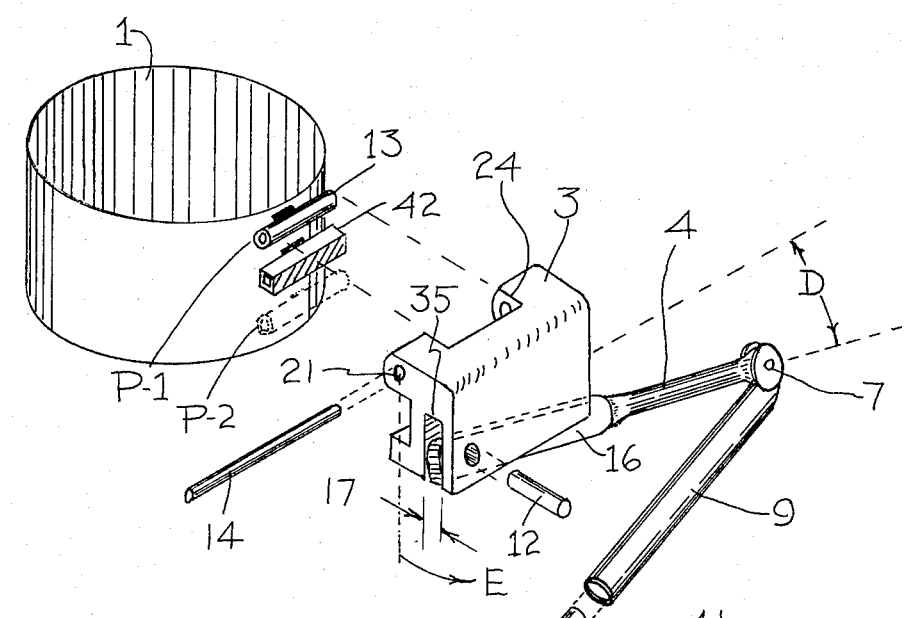
FIG. 5 is an exploded view of a complete linkage for the left side of the mouth made in accordance with the principles of the invention.

Further details of the invention will now be discussed with reference to FIGS. 5, 6 and 7. In FIG. 5, 1 and 1' represent a standard type of orthodontic band which is commonly used in the straightening of teeth. To each upper and lower band 1 and 1' is welded a rectangular archwire tube section 42 and 42' and a section of circular tube 13 and 13' in position $P_1$ or $P_2$. The rectangular tubes normally hold rectangular or circular archwires while the circular tubes normally serve for attaching externally mounted headgear. The archwires are strung from tooth to tooth in each dental arch to form the upper and lower force-exerting devices. The bands themselves are cemented to individual teeth as in everyday orthodontic practice. Two linkage assemblies made in accordance with the present invention, are mounted to four of these bands which have previously been cemented to upper and lower first molars on each side of the mouth.

Figure 6:
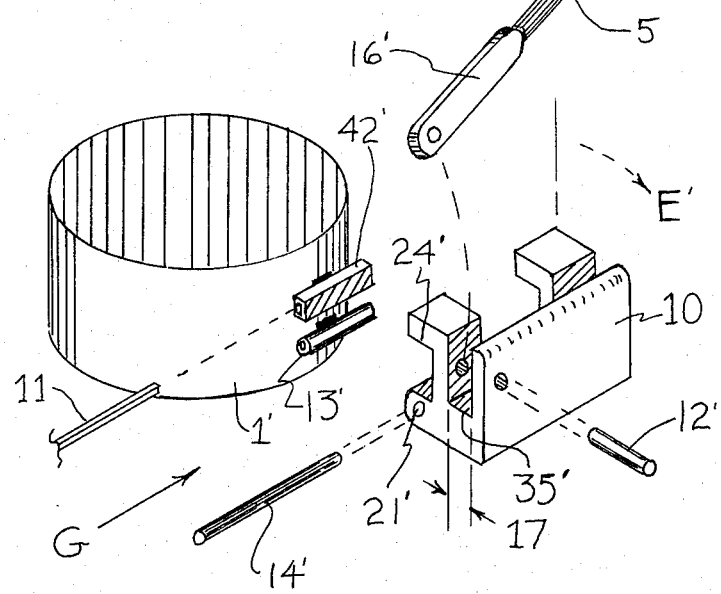
FIG. 6 is a partial frontal view of the linkage of FIG. 5 as seen from the direction G in FIG. 5.
Figure 6:
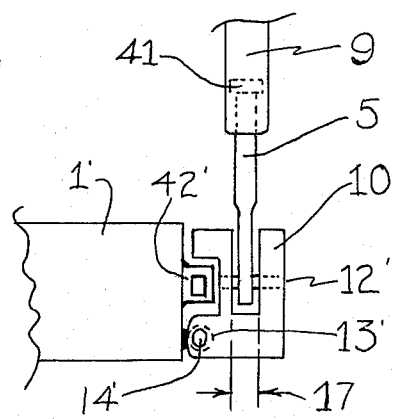

The upper and lower mounting blocks 3 and 10 shown in FIG. 5 and 6 contain slots 35 and 35'. Slot 35 holds the flattened portion 16 of the upper link 4. Slot 35' serves the same function for the flattened portion 16' of the piston 5. The flattened portions 16 and 16' are pivotably held in the blocks by means of fastening pins 12 and 12'. The slot width 17 is such as to permit sideways play of the link 4 and the piston 5 in mounting blocks 3 and 10, respectively. The cylinder 9 and upper link 4 are also loosely pivoted at point 37 as shown in FIG. 7.

The upper and lower mounting blocks 3 and 10 fit over the circular tubes 13 and 13' which, as explained above, are welded to the bands 1 and 1'. The circular tube 13 on the upper bands can be welded in position $P_1$ or $P_2$ to permit the desired or required fitting of the appliance to the tooth structure of a particular patient. Fastening pins 14 and 14' rotatably hold the mounting blocks to the bands and thus form hinge joints which permit the blocks to move in the directions E and E' (FIG. 5). The slots 24 and 24' shown in FIG. 5 allow movement of the blocks without interference with the rectangular tubes 42 and 42' and the arch wires entering and exiting them. This is an important feature of the invention because it permits the continuance of other orthodontic procedures while the orthopedic correction of the jaw is in progress. The presence of a full set of bands in the mouth is in fact an advantage because the inner surfaces of the bands, (i.e. on the lingual (tongue) side of the teeth) can be used for additional stabilization by anchoring the invention to other teeth as well as the molars and thus limit unfavorable tooth movements produced by the invention.

From the explanation given above, it will now be apparent that the upper stop of link 4 occurs when its flattened portion 16 comes to rest on the bottom of slot 35 during closure of the mouth. Piston 5, acting in combination with cylinder 9 and the hinge joint at point 7, converts part of the closing force to a horizontal component; the latter then produces forwrad displacement of the mandible.

The combination of loosely-fitting pinned members, plus the rotary freedom of the mounting blocks on their hinges allows considerable lateral freedom between upper and lower jaws. In addition, the telescoping feature of the linkage in cooperation with the hinge joint, permits a wider opening of the jaws than would a simpler bar linkage. The enlarged portion 41 of piston 5, plus the crimping of the cylinder 9 after assembly, prevents disengagement during wide opening of the mouth (FIG. 6). It is also possible to incorporate two concentric, telescoping cylinders into each linkage on both sides of the mouth to accommodate wider openings of the mouth when necessary.

Figure 7:
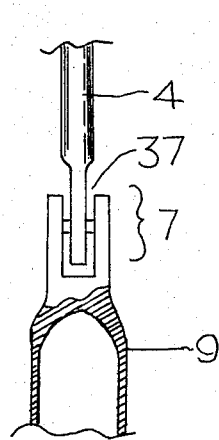
FIG. 7, a frontal view, shows in greater detail the pivot construction between the upper and lower portions of the hinge, illustrating the built-in lateral play of the joint.

FIG. 7 shows an enlarged view of the hinge at point 7. The clearance 37 further enhances the lateral freedom of the assembly.

Figure 8:
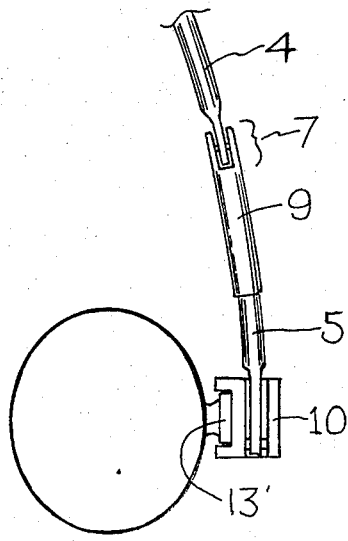
FIG. 8, a top view, illustrates a second embodiment of the invention.

In a second embodiment of the invention, the telescoping assembly is curved or angled along the horizontal plane of the cheek as is shown in FIG. 8. This arrangement would be useful in adding comfort where longer link elements are required (as might be the case, for example, in treating adults). The curvature of the assembly could minimize contact of the appliance with the inside of the cheek.

Adjustments of the appliance to the individual patient would be accomplished by choosing from a collection of telescoping hinge assemblies of different lengths. The orthodontist would thus be able to match an appliance to varying oral dimensions and also to adjust the amount of forward pressure during jaw closure.

Figure 9:
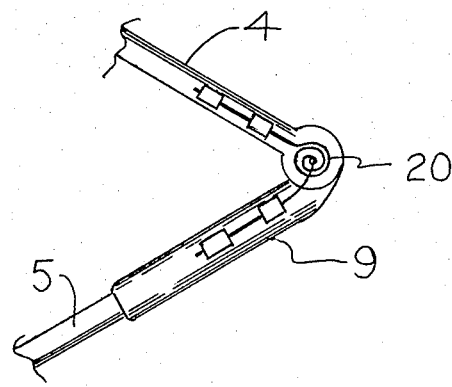
FIG. 9, a side view, depicts a third embodiment of the invention.

In the embodiment illustrated in FIG. 9 a spring 20 has been installed on the pivot 7. This spring biases the linkage to keep the mouth closed during sleep and thus maximize the time that corrective forces would be working on the mandible per day. It would also be possible to cover the linkages with thin, flexible tubing to further protect the inner surfaces of the mouth of sensitive patients.

Figure 10:
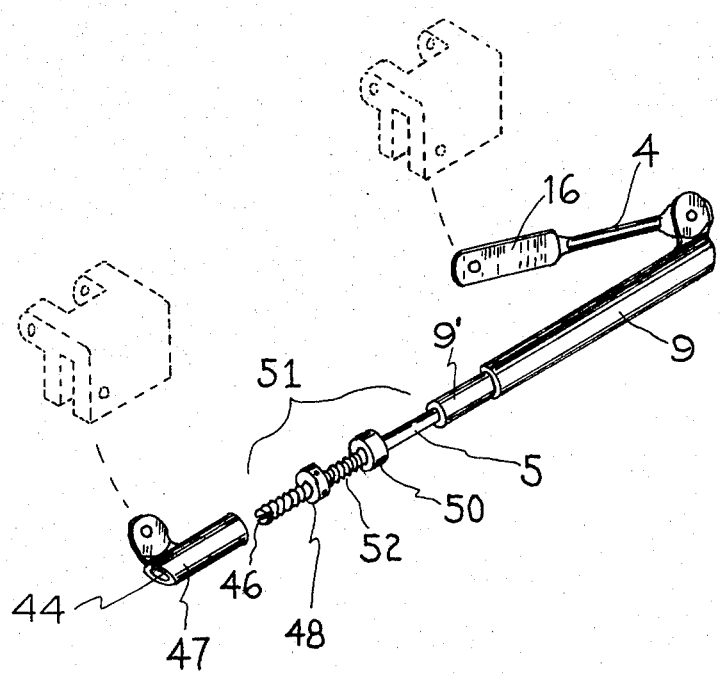
FIG. 10 is an exploded view of a fourth embodiment of the invention.
Figure 11:
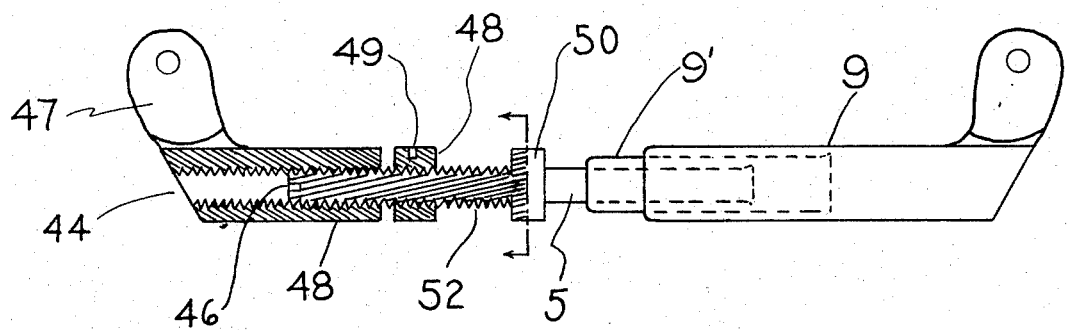
FIG. 11 is an enlarged cross section of the fourth embodiment.

With the embodiment shown in FIGS. 10 and 11 it is possible to adjust, in very fine increments, the allowable piston travel in the cylinder and thus better adapt the appliance to the needs of various patients. In this form of the invention, the piston 5 is incorporated in a joining assembly 51. The latter also includes a stop 50, a threaded portion 52 and a lock nut 48. The threaded portion mates with an internally threaded fixture 47. The cylinder 9 may incorporate one or more telescoping segments such as 9'. With the appliance assembled and in place in the mouth, the joining assembly 51 is turned until the desired point of path modification, point J in FIG. 2a, is reached. Turning of the joining assembly can be conveniently done by a small screwdriver applied to slot 46 through opening 44. Stop nut 48 is then positioned against the end of the threaded fixture by the use of a pin in hole 49. This locks the joining assembly against further turning. An advantage of this embodiment would be that it permits the orthodontist to adjust forward force on the mandible gradually as corrective "muscle-resting length" changes occurred. If multiple telescoping sections are used, the overall length of linkage components can be reduced but the assembly will still accommodate wide opening of the mouth. This advantage of multiple telescoping portions can, of course, be applied to other embodiments of the invention.

It is sometimes found that one or more first molars is missing in a particular patient. In these cases, another tooth may have begun to function as the missing one. Under these circumstances the invention, when attached to the applicable tooth, will serve the same purpose as previously described. A number of other variations and embodiments of the invention can now be devised by those skilled in the art. It is feasible, for example, to apply the linkages on the tongue side of the teeth where this may be of advantage.

It will thus be apparent that these and other embodiments and variations are possible without departing from the spirit of the invention.

I claim:

1. An intraoral dental appliance to improve a retrusive mandible orthopedically in the correction of Class II malocclusions comprising:
   (a) An upper pair of anchoring means each secured preferably to any upper teeth functioning as first molars on both the right and left sides of the mouth;
   (b) A lower pair of anchoring means each secured preferably to any lower teeth functioning as first molars on both right and left sides of the mouth.
   (c) A pair of upper mounting blocks pivotably attached to said upper pair of anchoring means;
   (d) A pair of lower mounting blocks pivotably attached to said lower pair of anchoring means;
   (e) A pair of relatively short links pivotably attached to said pair of upper blocks;
   (f) A pair of relatively long pistons pivotably attached to said pair of lower blocks;
   (g) A pair of cylinders each pivotably joined at one end to one of said upper links and each slidably enclosing on the other end one of said pistons, thus forming partially-telescoping, hinged couplings between the upper and lower rows of teeth on both sides of the mouth;

whereby closure of the mouth from an open position first causes uniform folding of the hinged couplings and simultaneous movement of the pistons into the cylinders until said relatively short links are fully seated within said upper blocks and then causes continued cylinder-piston closure and arcuate movement of the pistons so that a force is generated which moves the mandible forward, thus aligning the lower row of teeth with the upper row.

2. Intraoral dental appliances as described in claim 1 in which said upper and lower anchoring means are metal bands to which horizontal tube sections are rigidly joined to permit pivotble attachment of the upper and lower mounting blocks, said bands being cemented preferably to teeth functioning as upper and lower first molars.

3. Intraoral dental appliances as described in claim 1 in which said upper and lower mounting blocks contain vertical and horizontal slots to permit motion of the blocks without interference with existing orthodontic devices being concurrently employed.

4. Intraoral dental appliances as described in claim 1 in which the operating axes of the various pivoting arrangements as well as their looseness of fit permit the user to have lateral freedom of jaw movement while maintaining a forward force on the mandible at mouth closure.

5. Intraoral appliances for producing a forward force on the mandible of a person having retrusive mandible and lower occlusion, comprising two pairs of hinged, semi-collapsible two-bar linkages, one in each side of the mouth, each pivotably anchored through mounting blocks with are pre-positioned and cemented to bands on teeth functioning as the lower and upper first molars, said linkages having freedom of movement along a prescribed arc when the mouth is initially closing, freedom of movement laterally when side to side jaw movement occurs and a toggle action near closure, permitting closure forces to develop a horizontal force vector along the mandible to correct its retrusion and a spring bias to maximize the duration of corrective forces by maintaining them during periods when the wearer of the appliance is relaxed as, for example, during sleep.

6. Intraoral appliances for producing a forward and corrective force on the lower jaws of persons having retrusive mandibles comprising: upper and lower hinged blocks movably connected to bands cemented to upper and lower teeth, links extending from said upper hinged blocks and terminating at pivotably mounted cylinders, threaded fixtures rotatably attached to said lower hinged blocks and mating with partially-threaded pistons the unthreaded portions of which extend into the other end of said cylinders, whereby fine adjustment of the allowed piston-travel distance into the cylinder can be made by turning and locking the threaded portion of said partially-threaded piston within said threaded fixture thus altering the amount of corrective force applied to the mandible.

7. Intraoral dental appliances as described in claim 6 in which said pivotably-mounted cylinders contain independently slidble liners which increase the effective overall expanded length of the piston and cylinder and thus accommodate a desired width of mouth opening.

* * * * *